United States Patent
Park et al.

(10) Patent No.: US 11,452,994 B2
(45) Date of Patent: Sep. 27, 2022

(54) METHOD FOR PRODUCING PHOTOCATALYST AND PHOTOCATALYST FILTER FOR AIR CLEANING

(71) Applicants: Samsung Electronics Co., Ltd., Suwon-si (KR); POSTECH ACADEMY-INDUSTRY FOUNDATION, Pohang-si (KR)

(72) Inventors: Hee-Jin Park, Seoul (KR); Wonyong Choi, Pohang-si (KR); Seunghyun Weon, Seoul (KR); Sungwon Kim, Seoul (KR); Jee Yeon Kim, Seoul (KR)

(73) Assignees: Samsung Electronics Co., Ltd., Suwon-si (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 176 days.

(21) Appl. No.: 16/628,514

(22) PCT Filed: Aug. 8, 2018

(86) PCT No.: PCT/KR2018/009037
§ 371 (c)(1),
(2) Date: Jan. 3, 2020

(87) PCT Pub. No.: WO2019/031848
PCT Pub. Date: Feb. 14, 2019

(65) Prior Publication Data
US 2020/0179910 A1 Jun. 11, 2020

Related U.S. Application Data

(60) Provisional application No. 62/542,502, filed on Aug. 8, 2017.

(30) Foreign Application Priority Data

Aug. 6, 2018 (KR) ........................ 10-2018-0091235

(51) Int. Cl.
B01J 27/135 (2006.01)
B01J 23/42 (2006.01)
(Continued)

(52) U.S. Cl.
CPC ........ B01J 27/135 (2013.01); B01D 53/8609 (2013.01); B01D 53/8628 (2013.01);
(Continued)

(58) Field of Classification Search
None
See application file for complete search history.

(56) References Cited

U.S. PATENT DOCUMENTS 5,759,948 A   6/1998  Takaoka et al.
5,948,355 A * 9/1999  Fujishima .......... B01D 53/8603
                                                  422/4

(Continued)

FOREIGN PATENT DOCUMENTS

JP     2005-230645 A    9/2005
JP     4570637 B2      10/2010
(Continued)

OTHER PUBLICATIONS

Everly, Charles, et al. "Heterogeneous Photocatalytic Preparation . . . ". ASC. Communications to the Editor. 100:13 (1978) (Year: 1978).*

(Continued)

Primary Examiner — Sheng H Davis
(74) Attorney, Agent, or Firm — Jefferson IP Law, LLP

(57) ABSTRACT

Disclosed is a method for producing a photocatalyst for air cleaning. The present production method comprises the steps of: preparing titanium dioxide ($TiO_2$); attaching platinum to a surface of the titanium dioxide; and attaching (Continued)

fluoro to the platinum-attached surface of the titanium dioxide to obtain surface-modified titanium dioxide.

6 Claims, 12 Drawing Sheets

(51) Int. Cl.
 *B01D 53/86* (2006.01)
 *B01J 35/00* (2006.01)
 *B01J 35/02* (2006.01)
 *B01J 37/02* (2006.01)
 *B01J 37/34* (2006.01)

(52) U.S. Cl.
 CPC .......... *B01D 53/8668* (2013.01); *B01J 23/42* (2013.01); *B01J 35/004* (2013.01); *B01J 35/026* (2013.01); *B01J 37/024* (2013.01); *B01J 37/0221* (2013.01); *B01J 37/0228* (2013.01); *B01J 37/344* (2013.01); *B01D 2255/1021* (2013.01); *B01D 2255/20707* (2013.01); *B01D 2255/802* (2013.01); *B01D 2257/302* (2013.01); *B01D 2257/404* (2013.01); *B01D 2257/708* (2013.01)

(56) References Cited

U.S. PATENT DOCUMENTS

| | | | |
|---|---|---|---|
| 8,148,289 B2 | 4/2012 | Taniguchi et al. | |
| 8,367,050 B2 | 2/2013 | Taniguchi et al. | |
| 8,518,848 B2 | 8/2013 | Taniguchi et al. | |
| 8,986,906 B2 | 3/2015 | Jang et al. | |
| 2013/0172175 A1* | 7/2013 | Kim | B01J 35/1085 502/216 |
| 2014/0291142 A1* | 10/2014 | Jeon | C25B 1/55 204/242 |

FOREIGN PATENT DOCUMENTS

| | | | |
|---|---|---|---|
| JP | 5156009 B2 | | 3/2013 |
| JP | 2017009566 | * | 7/2015 |
| KR | 10-2009-0090194 A | | 8/2009 |
| KR | 10-2017-0009566 A | | 1/2017 |

OTHER PUBLICATIONS

Machine Translation of WO 2013/144385 (Year: 2012).*
Yuzawa, Hayato et al. "Direct Introduction of OH group to sp2-Carbon on Pt-loaded titanium oxide photocatalyst". Top Catal 57: 984-994 (2014) (Year: 2014).*
Jungwon Kim et al., "Simultaneous production of hydrogen with the degradation of organic pollutants using TiO2 photocatalyst modified with dual surface components", Energy Environ. Sci., Mar. 14, 2012, pp. 7647-7656.
Hyunwoong Park et al., "Effects of TiO2 Surface Fluorination on Photocatalytic Reactions and Photoelectrochemical Behaviors", J. Phys. Chem. B, School of Environmental Science and Engineering and Department of Chemistry, Pohang University of Science and Technology, Pohang, Korea, Jan. 5, 2004, pp. 4086-4093.
Jungwon Kim et al., "Synergic effect of simultaneous fluorination and platinization of TiO2 surface on anoxic photocatalytic degradation of organic compounds", Chem. Communication, Dec. 11, 2007, pp. 756-758.
Seunghyun Weon et al.,"Dual-components modified TiO2 with Pt and fluoride as deactivationresistant photocatalyst for the degradation of volatile organic compound", Elsevier, 2018.

* cited by examiner

METHOD FOR PRODUCING PHOTOCATALYST AND PHOTOCATALYST FILTER FOR AIR CLEANING

FIELD

The disclosure relates to a method for producing a photocatalyst, and a photocatalyst filter for air cleaning, and more particularly, to a method for producing a photocatalyst having improved resistance to photocatalytic deactivation, and a photocatalyst filter for air cleaning.

BACKGROUND

Because people spend 90% of their time indoors, lots of technology for disposing of indoor volatile organic compounds (VOCs) is receiving much attention. The indoor volatile organic compounds (VOCs) may be emitted from various materials such as furniture, decorations, and construction supplies. The presence of the volatile organic compounds (VOCs) may result in degraded quality of indoor environments and cause various types of health problems such as headache, allergy, nausea, and the like. An air filtration method may be used to improve the air quality, but the volatile organic compounds (VOCs) are adsorbed onto filtering media (e.g., activated carbon fibers), but are not degraded. Therefore, the volatile organic compounds (VOCs) adsorbed onto the filtering media have a problem in that they may be reemitted into the air from the filtering media when the filtering media are saturated. In this regard, photocatalytic degradation may be regarded as ideal technology for air cleaning because the photocatalytic degradation may be used to completely decompose the volatile organic compounds (VOCs) into innocuous carbon dioxide and water.

Among various photocatalysts, titanium dioxide ($TiO_2$) has been widely studied as the photocatalyst for environmental improvement because it is plentiful and inexpensive, and has excellent chemical and photochemical stability and high photooxidative power. Titanium dioxide generates radicals when it is exposed to ultraviolet rays. As a result, the titanium dioxide may kill microorganisms due to the strong oxidative power of these radicals, and degrade odor-causing substances that give out bad smells.

However, when titanium dioxide ($TiO_2$) is used for a long time, its photocatalytic activity may be deactivated. Deactivation of the photocatalysts often occurs when non-biodegradable intermediates and products are accumulated on surfaces of the photocatalysts. For example, air pollutants containing heteroatoms (Si, S, P, and N) may strongly bind to a surface of titanium dioxide ($TiO_2$) to produce inorganic matters causing the deactivation. The deactivation of the photocatalysts induced by the volatile organic compounds (VOCs) may be caused by strong adsorption and complexation of non-biodegradable carbonaceous intermediates generated in situ on surfaces of the photocatalysts.

Accordingly, there is a demand for a titanium dioxide ($TiO_2$) photocatalyst capable of retaining its activity even when used for a long time.

DISCLOSURE

Technical Problem

The disclosure provides a method for producing a photocatalyst having improved resistance to photocatalytic deactivation, and a photocatalyst filter for air cleaning.

Technical Solution

A method for producing a photocatalyst for air cleaning according to one embodiment of the disclosure includes preparing titanium dioxide ($TiO_2$), attaching platinum to a surface of the titanium dioxide, and attaching a fluoro to the platinum-attached surface of the titanium dioxide to obtain surface-modified titanium dioxide.

In the attaching of the platinum to the surface of the titanium dioxide, the platinum may be attached to the surface of the titanium dioxide using a photodeposition method, and, in the obtaining of the surface-modified titanium dioxide, the platinum-attached titanium dioxide may be put into a fluoride solution to attach the fluoro to the platinum-attached surface of the titanium dioxide.

Meanwhile, the prepared titanium dioxide may be in a powder form, and the attaching of the platinum to the surface of the titanium dioxide may include attaching the platinum to the surface of the titanium dioxide in the powder form using a photodeposition method.

In this case, the production method according to this embodiment may further include mixing the platinum-attached titanium dioxide in the powder form with a volatile solvent to prepare a paste, and spreading the paste on a substrate and then drying the substrate, and, in the obtaining of the surface-modified titanium dioxide, the dried substrate may be put into a fluoride solution.

Meanwhile, the fluoride solution may be an NH4F solution, a NaF solution, a KF solution, or an HF solution.

Meanwhile, the attaching of the fluoro to the platinum-attached surface of the titanium dioxide may include replacing a hydroxyl group in the platinum-attached surface of the titanium dioxide with a fluoro.

Meanwhile, the production method according to this embodiment may further include manufacturing the obtained surface-modified titanium dioxide into a bead shape.

Meanwhile, the production method according to this embodiment may further include coating a porous material with the obtained surface-modified titanium dioxide.

Meanwhile, a photocatalyst filter for air cleaning according to one embodiment of the disclosure includes surface-modified titanium dioxide (surface-modified $TiO_2$), and the surface-modified titanium dioxide is obtained by separately attaching platinum and a fluoro to a surface of titanium dioxide.

In this case, the photocatalyst filter according to this embodiment may further include a casing, and the casing may be filled with the surface-modified titanium dioxide in a bead shape.

Meanwhile, the photocatalyst filter according to this embodiment may further include a porous material, and the porous material may be coated with the surface-modified titanium dioxide.

BEST MODE

Figure 1:
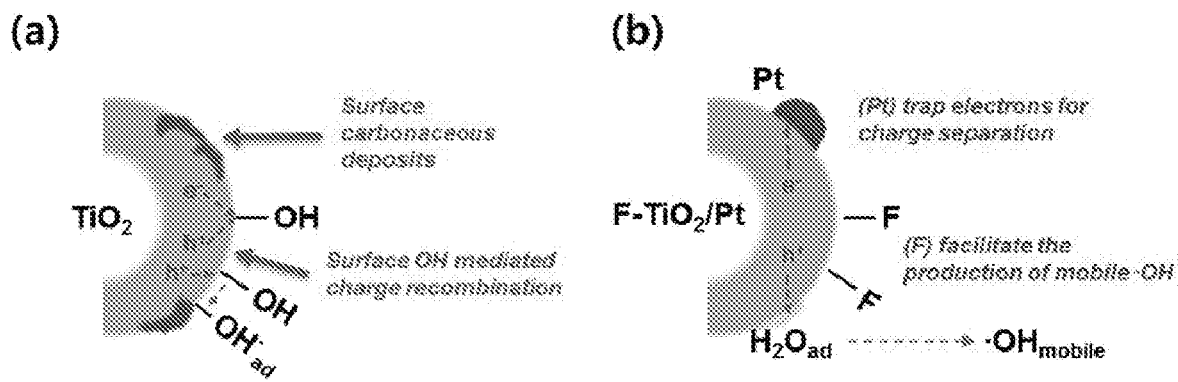
FIG. 1 is a diagram showing a photocatalytic degradation mechanism which occurs in $TiO_2$ whose surface is not modified (Bare $TiO_2$) and F—$TiO_2$/Pt in which a $TiO_2$ surface is modified with a fluoro and platinum.

In describing the disclosure, detailed descriptions with respect to known functions or constructions of the disclosure will be omitted when the detailed descriptions are considered to make the gist of the disclosure unclear. And, the terms used hereinafter are terms defined in consideration of their functions in the disclosure, and thus may be varied according to the intention or relationship of users, operators, and the like. Therefore, the definitions of the terms will be made based on the contents throughout this specification.

Although the terms first, second, etc. may be used to describe various elements, these elements are not limited by these terms. These terms are only used to distinguish one element from another.

The terminology used in the disclosure is for the purpose of describing particular embodiments only and is not intended to be limiting of exemplary embodiments. The singular forms "a," "an" and "the" are intended to include the plural forms as well, unless the context clearly indicates otherwise. It should be understood that the terms "comprises," "comprising," "includes" and/or "including," when used in this specification, specify the presence of stated features, integers, steps, operations, elements, components and/or combinations thereof, but do not preclude the presence or addition of one or more other features, integers, steps, operations, elements, components and/or combinations thereof.

The terms used herein are used for the purpose of describing particular embodiments only and are not intended to limit the scopes of other exemplary embodiments. The singular forms "a," "an" and "the" are intended to include the plural forms as well, unless the context clearly indicates otherwise. All the terms (including technical and scientific terms) used herein have the same meaning as commonly understood by one of ordinary skill in the art to which the disclosure pertains. It will be further understood that the terms, such as those defined in commonly used dictionaries, should be interpreted as having a meaning that is consistent with or similar to their meaning in the context of the relevant art and will not be interpreted in an idealized or overly formal sense unless expressly so defined herein. In some cases, even the terms defined in the specification are not intended to be interpreted to exclude the embodiments of the disclosure.

Hereinafter, the embodiments of the disclosure will be described in detail in order to enable those of ordinary skill in the art to which the disclosure pertains to embody and practice the disclosure. However, the disclosure is not limited to the embodiments disclosed below, but can be implemented in various forms. In the drawings, the description of parts regardless of the detailed description will be omitted in order to describe the disclosure more clearly. Throughout this specification, like parts are designated by like reference numerals.

The disclosure relates to a photocatalyst. The photocatalyst may induce a chemical reaction using light energy to kill various pathogens and bacteria in the air, may remove toxic substances in the air, such as nitrogen oxides ($NO_X$), sulfur oxides ($SO_X$), formaldehyde, toluene, and the like, may degrade malodorous substances such as acetaldehyde, ammonia, hydrogen sulfide, and the like, and may decomposes organic substances such as cigarette smoke, oil sludge, and the like. Also, the photocatalyst may remove gases, and may also remove dust, and the like by electrically charging the dust, and the like with produced photoelectrons.

Materials that may be used as this photocatalyst, for example, include titanium dioxide ($TiO_2$), silicon dioxide ($SiO_2$), vanadium oxide ($V_2O_3$), zinc oxide (ZnO), zirconium oxide ($ZrO_2$), cadmium sulfide (CdS), tungsten oxide ($WO_3$), and the like. Among these, the titanium dioxide is also preferred because the titanium dioxide has high photocatalytic activity.

When titanium dioxide is illuminated by light, electrons (e−) and holes (h+) are generated. Then, the electrons (e−) reacts with surface-adsorbed oxygen to produce $O_2-$ (superoxide anions), and the holes (h+) reacts with surface-adsorbed oxygen to produce hydroxides (OH radicals) having a strong action of oxidation. The titanium dioxide exerts antifoulant, antibacterial, germicidial, deodorant, toxic substance-removal, air pollutant-reducing, and superhydrophilic effects through this oxidation reaction.

The photocatalyst according to embodiments of the disclosure may include titanium dioxide as a basic component.

When titanium dioxide is used for a long period of time, the titanium dioxide may be deactivated by various factors. A degree of photocatalytic deactivation may vary depending on various conditions (e. g., the mass and surface property of a photocatalyst, the concentration and type of a substrate, a level of humidity, the $O_2$ concentration, the intensity of light, and the type of a photoreactor). As the non-biodegradable intermediates generated by degradation of the volatile organic compounds (VOCs) are accumulated, the photocatalyst may be deactivated.

Meanwhile, the titanium dioxide may be surface-modified to enhance resistance to its deactivation. The term "surface modification" means that a new property is formed on a surface of a material to endow the material with desired functions.

The titanium dioxide photocatalyst according to embodiments of the disclosure is surface modified to enhance resistance to deactivation thereof. In particular, the photocatalyst according to the embodiments of the disclosure is obtained by surface-modifying a surface of titanium dioxide with two components, that is, platinum (Pt) and fluoride, and thus has a shape in which platinum and a fluoro (F) are separately attached (or loaded) to a surface of titanium dioxide. Deactivation of the photocatalyst may be effectively prevented through a synergistic action of the two components, that is, platinum and a fluoro, which are attached to the surface of the titanium dioxide.

Surface fluorination of titanium dioxide may occur via the exchange between a fluoro and a hydroxyl group on a surface of titanium dioxide. This is a typical ligand exchange reaction (Reaction Formula (1)). Fluorinating a surface of titanium dioxide does not cause any change in crystal structure or light absorbance of the titanium dioxide but remarkably improves light-induced hydrophilicity and remarkably enhances adsorption of water molecules. The titanium dioxide whose surface is fluorinated hinders adsorption of organic compounds, but promotes production of mobile OH radicals because the transfer of holes to molecularly adsorbed $H_2O$ (which causes production of the mobile OH radicals) (Reaction Formula (2)) occurs more readily compared to the transfer of holes to surface hydroxyl groups (which causes binding of the OH radicals to the surfaces thereof) (Reaction Formula (3)) since an amount of the hydroxyl groups on the surface of the titanium dioxide is reduced. The holes converted into the mobile OH radicals on the fluorinated surface of the titanium dioxide are less affected by the recombination with CB electrons (Reaction Formula (4)). As a result, more holes may be used for an oxidation reaction.

>Ti—OH+F⁻⇌>Ti—F+OH⁻     Reaction Formula (1)

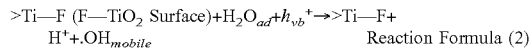

>Ti—F (F—TiO₂ Surface)+H₂O$_{ad}$+h$_{vb}^+$→>Ti—F+ H⁺+.OH$_{mobile}$     Reaction Formula (2)

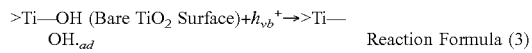

>Ti—OH (Bare TiO₂ Surface)+h$_{vb}^+$→>Ti— OH.$_{ad}$     Reaction Formula (3)

>Ti—OH.$_{ad}$+e$_{cb}^-$→>Ti—OH     Reaction Formula (4)

The photocatalystic VOC degradation starts to occur on an active surface of titanium dioxide on which oxidant radicals are produced. Meanwhile, VOC degradation intermediates are accumulated on the surface of the titanium dioxide, which may induce accumulation of non-biodegradable carbonaceous materials and subsequent deactivation of catalytic surfaces thereof. On the other hand, when the mobile OH radicals are produced, the accumulation of the non-biodegradable intermediate may be considerably delayed because the oxidant radicals may move from an active site to a remote surface site on which the degradation intermediates may be accumulated. This remote photocatalytic oxidation mediated by the mobile OH radicals is more effective in preventing the catalytic deactivation caused by in situ deposition of the carbonaceous intermediates, compared to the photocatalytic oxidation mediated by the surface-bound OH radicals. This adsorption of the degradation intermediates onto the fluorinated surface of the titanium dioxide may be hindered.

And, when additional platinum is present on a surface of the titanium dioxide, the lifespan of photo-generated electrons may be extended so that more holes can react with adsorbed water molecules.

As a result, when the titanium dioxide is surface-modified to have both Pt and a fluoro present on the surface thereof, the titanium dioxide may exert synergy in effectively preventing the catalytic deactivation caused by the accumulation of the degradation intermediates.

A photocatalytic degradation mechanism which occurs in TiO2 whose surface is not modified (Bare TiO2) and F—TiO2/Pt in which a surface of TiO2 is modified with a fluoro and platinum is shown in FIG. 1.

In the Bare TiO2, VB holes mainly react with hydroxyl groups on the surface of the Bare TiO2 to produce surface-bound OH radicals (Reaction Formula (3)), but the holes collected in the surface hydroxyl groups may easily re-bind to CB electrons (Reaction Formula (4)), thereby limiting reactivity of the surface-bound OH radicals. However, when the surface hydroxyl group is replaced with a fluoro so that the fluoro is attached to titanium dioxide, a density of the surface hydroxyl group is reduced, resulting in increased ratio of the holes reacting with the adsorbed water molecules (mobile OH radicals are produced: Reaction Formula (2)) and decreased ratio of the holes reacting with the surface hydroxyl groups (surface-bound OH radicals are produced: Reaction Formula (3)). Light-induced hydrophilicity of F—TiO₂ promotes a reaction of the holes with the adsorbed water molecules. On the other hand, the role of surface-attached Pt is to capture electrons while the holes are reacting with the adsorbed water molecules. As a result, when both Pt and F species are present on the titanium dioxide, a larger number of the mobile OH radicals are produced on a surface of F—TiO₂/Pt, which may enhance the photocatalytic activity during the VOC degradation and improve the resistance to the catalytic deactivation.

The surface-modified photocatalyst according to an embodiment of the disclosure may be used in various fields. According to one embodiment, the photocatalyst according to an embodiment of the disclosure may be applied to filters for an air purifying apparatus.

The air purifying apparatus is an apparatus for purifying air within the building, and is mainly installed in common homes, offices, and the like to collect dust floating in the air, or used to remove gases as well as such dust collection. The air purifying apparatus may mean all types of devices having a function of purifying the air. For example, the air purifying apparatus may be realized as an apparatus capable of fulfilling complex functions, such as an apparatus used for the purpose of air purification only, an air conditioner having an air cleaning function, a humidifier having an air cleaning function, and the like.

The photocatalyst according to the embodiment of the disclosure may be applied to a photocatalyst filter equipped in the air purifying apparatus. The photocatalyst filter may be manufactured in various shapes. For example, the photocatalyst filter may be manufactured in shapes such as foil, mesh, fiber, film, sheet, and the like.

As one example, the surface-modified photocatalyst according to the embodiment of the disclosure may be coated onto a porous material, manufactured into bead shapes, or compressed into honeycomb structures, which may be used as a material for photocatalyst filters. The surface-modified photocatalyst may be used as a base material to manufacture filters, but the titanium dioxide may be first used to manufacture basic filter structures such as porous materials, beads, honeycombs, and the like, and then to fluorinate and platinize surfaces of the basic filter structures in order to minimize an amount of expensive Pt used.

Figure 2:
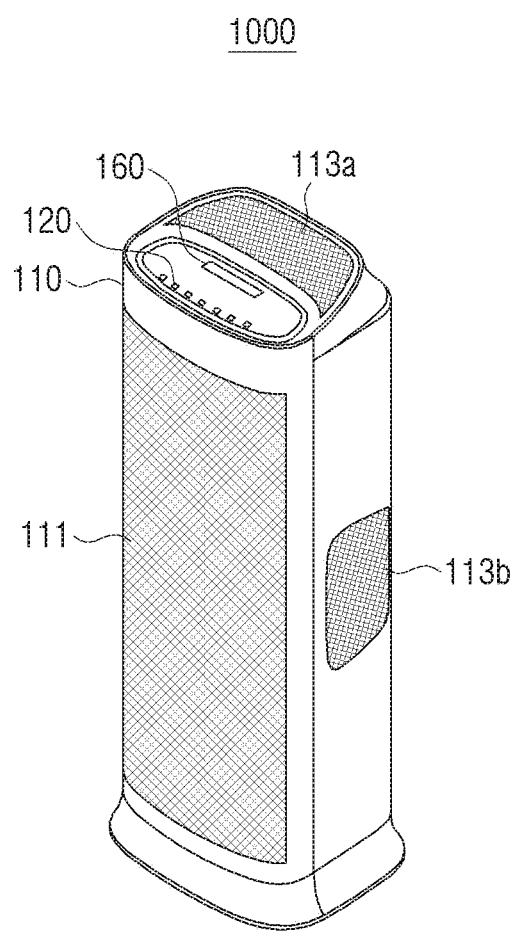
FIG. 2 is a diagram showing an air purifying apparatus according to one embodiment of the disclosure.

FIG. 2 is a diagram showing an air purifying apparatus according to one embodiment of the disclosure. Referring to FIG. 2, an air purifying apparatus 1000 may include a body 110 configured to form an appearance thereof, an inlet port 111 configured to suck in the air from an indoor space, outlet ports 113a and 113b configured to discharge the air which has been purified after flowing in the indoor space, an input unit 120, and a display unit 160 configured to display an operating status of the air purifying apparatus 1000.

The input unit 120 may include buttons configured to input various types of control information associated with the air purifying apparatus 1000, such as a power button configured to turn on or off the air purifying apparatus 1000, a timer button configured to set a running time of the air purifying apparatus 1000, a lock button configured to limit the handling of the input unit in order to prevent the malfunction of the input unit, and the like. In this case, each of the input buttons may be a push or membrane switch configured to generate an input signal when a user presses the button, or a touch switch configured to generate an input signal when a user touches part of his/her own body.

When the input unit 120 uses a touch switch mode, the input unit 120 may also be realized to be integrated with the display unit 160.

The display unit 160 may display information on the status of the air purifying apparatus 1000. For example, the display unit 160 may display information on a pollution degree of filters in the air purifying apparatus 1000, information on a replacement time of the filters, and information on current activities (for example, information on whether it is air quality-sensing step or a filtering step, information on a direction of air flow). Meanwhile, according to another embodiment, such information may be provided to external devices such as smartphones communicating with the air purifying apparatus 1000.

Figure 3:
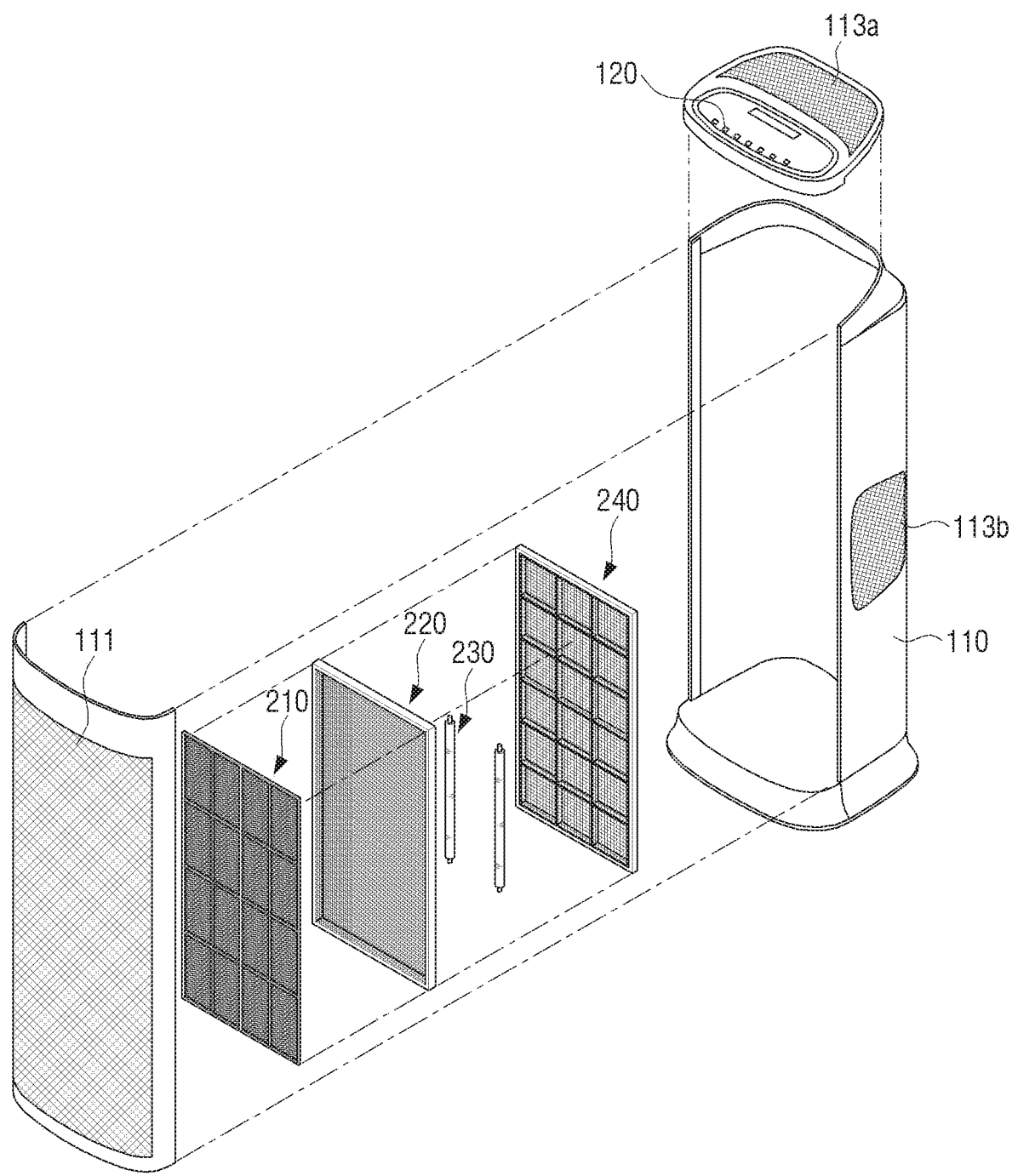
FIG. 3 is a diagram showing an inside configuration of the air purifying apparatus according to one embodiment of the disclosure.

FIG. 3 is a schematic exploded perspective view of the air purifying apparatus 1000 according to one embodiment of the disclosure.

Referring to FIG. 3, the air purifying apparatus 1000 may include a pre-filter 210, a HEPA filter 220, a light source unit 230, and a photocatalyst filter 240 inside the body 110. Although not shown, the air purifying apparatus 1000 may further include a deodorizing filter including activated charcoal between the pre-filter 210 and the HEPA filter 220. An array order of the filters may follow the order as shown in FIG. 3, but the other array orders may also be available.

Also, the number of filters is not limited to the number of filters shown in FIG. 3. Some of the configurations may be omitted according to the embodiments, and, although not shown, the proper levels of the configurations apparent to those skilled in the art may be further included in the air purifying apparatus 1000.

Although not shown, the air purifying apparatus 1000 may include at least one fan configured to allow the air distributed in an indoor space to flow inside the body 110 through the inlet port 111. The air flowing in through the inlet port 111 passes through the filters to filter impurities in the air.

Relatively larger dust particles are primarily filtered through the pre-filter 210. The HEPA filter 220 is configured to filter fine dust, and the like which have not been filtered through the previous filter. For example, the HEPA filter 220 may be formed of glass fibers.

The light source unit 230 may emit light from a suitable light source to cause a photocatalytic reaction in the photocatalyst constituting the photocatalyst filter 240. For example, the light source unit 230 may be realized as diodes or LEDs such as a fluorescent lamp, incandescent lamp, and the like, and may emit light having a wavelength range of white light, red light, green light, blue light, ultraviolet rays, visible rays, infrared rays, NIR (0.75 to 1.4 μm), SWIR (1.4 to 3 μm), MWIR (3 to 8 μm), LWIR (8 to 15 μm), FIR (15 to 1,000 μm), or the like.

Although the light source unit 230 arranged on one surface of the photocatalyst filter 240 is shown in FIG. 3, but is not particularly limited to this layout type. In this case, the light source unit 230 may be provided in each of both surfaces of the photocatalyst filter 240. Also, the light source unit 230 is not necessarily arranged to face the photocatalyst filter 240, but may be arranged in a proper position to irradiate the photocatalyst filter 240 with light.

The photocatalyst filter 240 may be a filter to which the surface-modified photocatalyst according to an embodiment of the disclosure is applied. For example, the photocatalyst filter 240 includes surface-modified titanium dioxide, wherein the surface-modified titanium dioxide may be obtained by separately attaching platinum and a fluoro to a surface of titanium dioxide. When the photocatalyst filter 240 includes a porous material, the porous material may be coated with the surface-modified titanium dioxide. When the photocatalyst filter 240 includes a casing configured to accommodate a bead-type photocatalyst, the casing may be filled with the bead-shaped, surface-modified titanium dioxide. As another example, a honeycomb structure manufactured by pressing the surface-modified titanium dioxide may be included in the photocatalyst filter 240.

Figure 4:
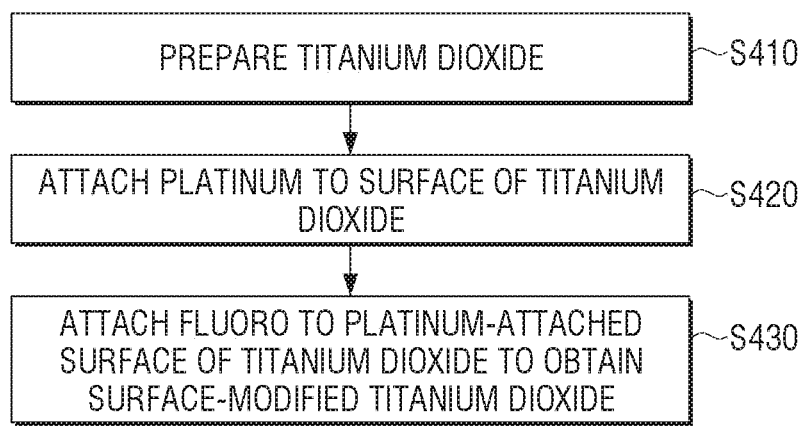
FIG. 4 is a flow chart for explaining a method for producing a photocatalyst for air cleaning according to one embodiment of the disclosure.

FIG. 4 is a flow chart for explaining a method for producing a photocatalyst for air cleaning according to one embodiment of the disclosure.

Referring to FIG. 4, first of all, titanium dioxide ($TiO_2$) is prepared (S410). In this case, the titanium dioxide may be in the form of a powder, foil, mesh, a fiber, a film, a sheet, a honeycomb, a porous material, and the like.

Then, platinum is attached to a surface of the titanium dioxide (S420). Then, a fluoro is attached to a platinum-attached surface of the titanium dioxide to obtain surface-modified titanium dioxide (S430).

Meanwhile, as described above, platinum is first attached to a surface of the titanium dioxide, and a process of attaching the fluoro may be performed in a sequential manner. However, according to another embodiment, the fluoro is attached to a surface of the titanium dioxide, and a process of attaching the platinum may be then performed.

To attach platinum to a surface of the titanium dioxide (or the fluoro-attached titanium dioxide), a photodeposition method may be used. For photodeposition, a mixed solution including titanium dioxide and a platinum precursor may be irradiated with ultraviolet rays. For example, compounds, which contain a halogen element such as chloroplatinic acid ($H_2PtCl_6$), and the like or do not include a halogen element such as a nitrate of platinum, an amine (e. g., dinitrotetramine platinum ($Pt(NH3)_4(NO_3)_2$)), and the like, may be used as the platinum precursor. Platinum nanoparticles may be attached to a surface of the titanium dioxide using a photodeposition method.

To attach the fluoro to a surface of the titanium dioxide (or the platinum-attached titanium dioxide), the titanium dioxide may be put into a fluoride solution for a predetermined period of time (for example, 30 minutes to 1 hour), and may be subjected to a reaction process. For example, an $NH_4F$ solution, a NaF solution, a KF solution, an HF solution may be used as the fluoride solution.

According to one embodiment, the platinum-attached titanium dioxide in the powder form may be mixed with a volatile solvent to prepare a paste, and the paste may be spread on a substrate, and then dried. The dried substrate may be put into a fluoride solution to obtain surface-modified titanium dioxide. In this case, the volatile solvent may be a solvent such as ethanol, isopropyl alcohol, acetone, or the like.

Hereinafter, embodiments of the disclosure will be described to aid in understanding the disclosure. In this case, the following embodiments are intended to encompass Examples and Comparative Examples according to the disclosure. However, it should be understood that the embodiments provided hereinafter are merely illustrative for better understanding, but are not intended to limit the scope of the disclosure.

1. Production of Photocatalyst

Example 1: F—$TiO_2$/Pt $TiO_2$ having a surface to which platinum (Pt) was attached was obtained using a photodeposition method. Specifically, chloroplatinic acid ($H_2PtCl_6$) serving as a platinum (Pt) precursor, and methanol (1 M) serving as an electron donor were added to an aqueous suspension of $TiO_2$ (P25) having an average surface area of 50 $m^2$/g and a primary particle size of 20 to 30 nm. For photodeposition, the suspension was irradiated with a 200-W mercury lamp for 30 minutes. The Pt/$TiO_2$ powder was collected by filtration, and washed with deionized water. For a degradation experiment of volatile organic compounds (VOCs), a glass substrate (2×2 $cm^2$) was coated with a Pt/$TiO_2$ powder using a doctor-blade method. The photocatalyst powder was thoroughly mixed with ethanol at a concentration of 0.15 g $TiO_2$/mL. The mixed paste was spread on the glass substrate, dried in the air, and then heated at 200° C. for 2 hours to remove residual ethanol. For surface fluorination, an aqueous solution of NaF (pH 3.5) was prepared. The Pt/$TiO_2$-coated film was immersed in a NaF solution for 30 minutes, and dried in the air to produce F—$TiO_2$/Pt.

Comparative Example 1: Bare $TiO_2$

For degradation experiment of volatile organic compounds (VOCs), a glass substrate (2×2 $cm^2$) was coated with a $TiO_2$ powder using a doctor-blade method. The photocatalyst powder was thoroughly mixed with ethanol at a concentration of 0.15 g $TiO_2$/mL. The mixed paste was spread on the glass substrate, dried in the air, and then heated at 200° C. for 2 hours to remove residual ethanol, thereby producing Bare $TiO_2$.

Comparative Example 2: F—$TiO_2$

For degradation experiment of volatile organic compounds (VOCs), a photocatalyst powder was thoroughly mixed with ethanol at a concentration of 0.15 g $TiO_2$/mL. The mixed paste was spread on a glass substrate, dried in the air, and then heated at 200° C. for 2 hours to remove residual ethanol. For surface fluorination, an aqueous solution of NaF (pH 3.5) was prepared. The $TiO_2$-coated film was immersed in a NaF solution for 30 minutes, and dried in the air to produce F—$TiO_2$.

Comparative Example 3: Pt/$TiO_2$ $TiO_2$ having platinum (Pt) attached to a surface thereof was obtained using a photodeposition method. Specifically, chloroplatinic acid ($H_2PtCl_6$) serving as a platinum (Pt) precursor, and methanol (1 M) serving as an electron donor were added to an aqueous suspension of $TiO_2$ (P25) having an average surface area of 50 $m^2$/g and a primary particle size of 20 to 30 nm. For photodeposition, the suspension was irradiated with a 200-W mercury lamp for 30 minutes. The Pt/$TiO_2$ powder was collected by filtration, and washed with deionized water. For a degradation experiment of volatile organic compounds (VOCs), a glass substrate (2×2 $cm^2$) was coated with a Pt/$TiO_2$ powder using a doctor-blade method. The photocatalyst powder was thoroughly mixed with ethanol at a concentration of 0.15 g $TiO_2$/mL. The mixed paste was spread on the glass substrate, dried in the air, and then heated at 200° C. for 2 hours to remove residual ethanol, thereby producing Pt/$TiO_2$.

2. Material Characterization

A high-resolution transmission electron microscope (HR-TEM, JEOL, JEM-2200FS) having a Cs calibration and electron energy loss spectrum (EELS) was used to characterize an element distribution of F—$TiO_2$/Pt.

A surface atomic composition of F—$TiO_2$/Pt was measured by an X-ray photoelectron spectroscopy (XPS) (Theta Probe AR-XPS System) using Al Kα rays (1,486.6 eV) as an excitation source.

A spectrofluorometer (HORIBA fluoromax-4) was used to analyze the fluorescence emission (excited at 332 nm) of 7-hydroxycoumarin (having a central emission at 450 nm) that would be generated as a result of remote photocatalytic reaction of mobile OH radicals with coumarin.

Secondary ion mass spectroscopy (SIMS, CAMECA, IMS 6F, $O_2$+ Gun) was used to analyze carbonaceous residues accumulated on a surface of each of the photocatalysts (F—$TiO_2$/Pt, Pt/$TiO_2$, F—$TiO_2$, and Bare $TiO_2$).

The absorption spectrum of each of the photocatalysts was measured using a diffuse reflectance UV-visible absorption spectrophotometer (Shimadzu UV-2401PC).

3. Characterization of Photocatalysts

Figure 5:
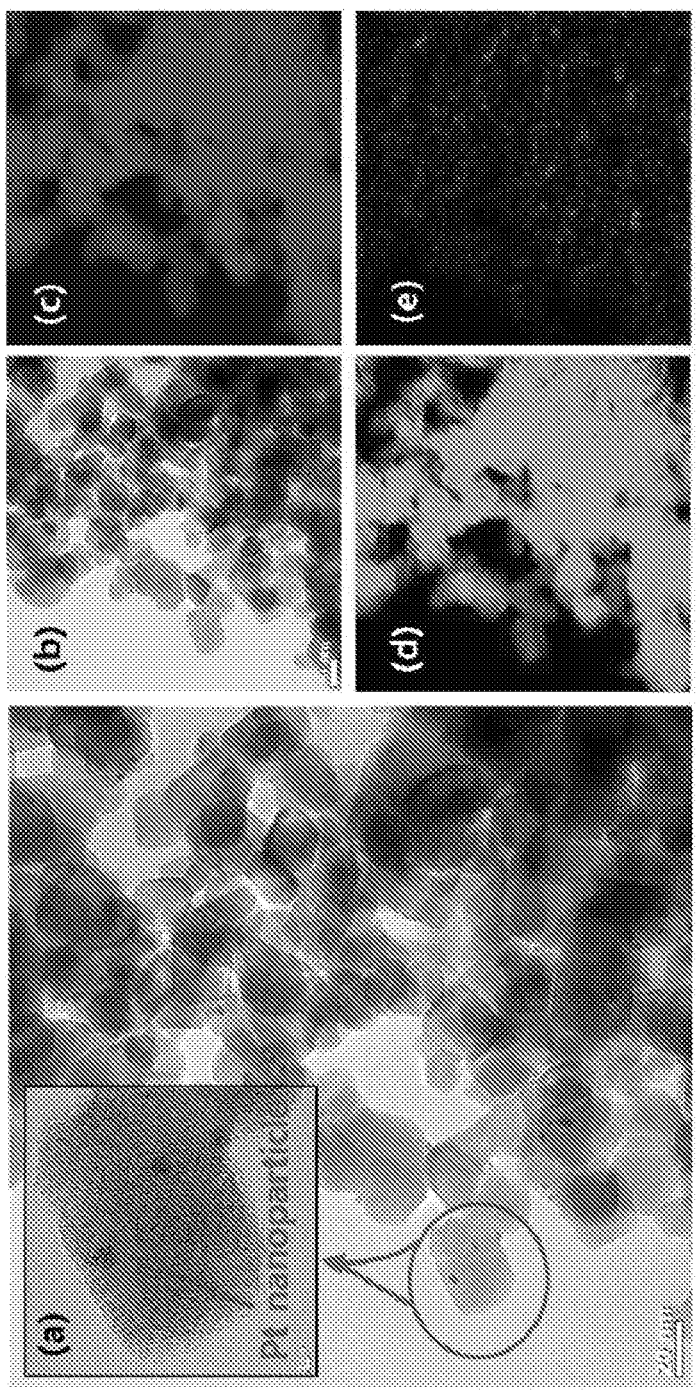
FIG. 5 shows (a) an HR-TEM image, (b) a zero-loss filtering image, (c) an EELS mapping image (Ti), (d) an EELS mapping image (O), and (e) an EELS mapping image (F) of F—$TiO_2$/Pt.
Figure 6:
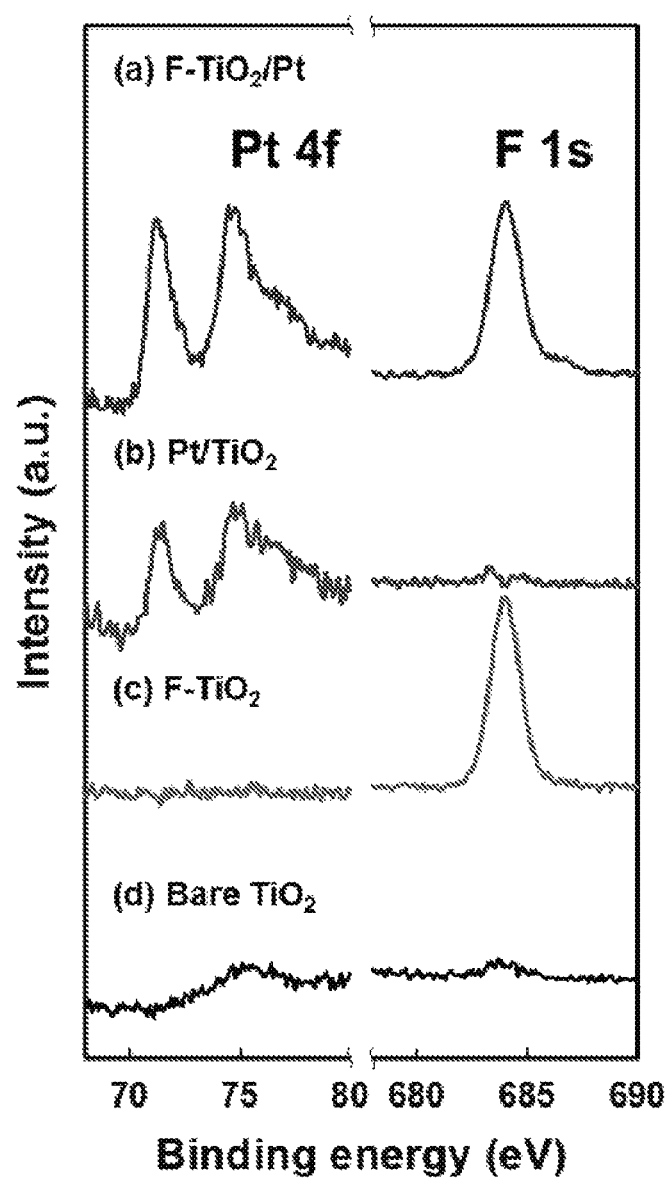
FIG. 6 shows (a) a Pt 4f and F 1s band at XPS spectra of F—$TiO_2$/Pt, (b) a Pt 4f and F 1s band at XPS spectra of Pt/$TiO_2$, (c) a Pt 4f and F 1s band at XPS spectra of F—$TiO_2$, and (d) a Pt 4f and F 1s band at XPS spectra of Bare $TiO_2$.

An element distribution of Ti, O, F and Pt in the F—$TiO_2$/Pt film was determined by HR-TEM and EELS assays (FIG. 5). It was confirmed that the platinum nanoparticles having as size of 1 to 3 nm were clearly attached to a surface of $TiO_2$ ((a) of FIG. 5). Elementary F spots were distributed on a surface of $TiO_2$ ((e) of FIG. 5). From these results, it can be seen that a surface of the F—$TiO_2$/Pt film was clearly fluorinated. From an XPS assay, it was confirmed that Pt and F were present on a surface of each of the photocatalyst films (FIG. 6). Peaks having a binding energy of 71.28 eV and 74.45 eV correspond respectively to $4f_{7/2}$ and $4f_{5/2}$ bands of metallic platinum attached to the $TiO_2$ surface. A peak having a binding energy of 684 eV correspond to a peak of F adsorbed onto the $TiO_2$ surface. Both Pt and F signals were observed for F—$TiO_2$/Pt, indicating that Pt and F coexisted on the $TiO_2$ surface.

4.1 Measurement of Photocatalytic Activity

A degradation experiment of volatile organic compounds (VOCs) was performed under ambient conditions in a closed circulation reactor (see S. Weon, W. Choi, Environ. Sci. Technol. 50 (2016) 2556). The photocatalyst films of $TiO_2$ (Comparative Example 1), F—$TiO_2$ (Comparative Example 2), Pt/$TiO_2$ (Comparative Example 3), and F—$TiO_2$/Pt (Example 1) under the same experimental conditions for photocatalytic degradation of toluene (the other VOCs were usable instead of toluene). A Pyrex glass reactor (having a volume of approximately 300 mL) with a quartz window (having a radius of 3 cm), and an optoacoustic gas monitor (LumaSense, INNOVA, 1412i) were connected to a Teflon tube (having a radius of 2 mm). A magnetic bar was disposed inside the reactor to circulate the air. A 370 nm emitting UV-LED (Luna Fiber Optic Korea, ICN14D-096) was used as a light source. The intensity of ultraviolet light was measured for a surface of the photocatalyst using a power meter (Newport, 1815-C). As a result, the intensity of ultraviolet light was 12 $mW/cm^2$. The optoacoustic gas monitor was able to measure concentrations of toluene, carbon dioxide, and water vapor at the same time. Relative humidity (RH) was controlled to approximately 65% by bubbling air through a stainless steel bottle containing deionized water. Before each experiment, the reactor was pursed with high-purity air, and a photocatalyst film was pre-washed for an hour under UV illumination to remove organic impurities adsorbed onto the photocatalyst film. After the pre-washing, a standard gas (300 ppmv of toluene in Ar as a carrier gas) was diluted with high-purity air to adjust a concentration of toluene. For a degradation experiment, an initial concentration of toluene was adjusted to 50 ppmv.

Figure 7:
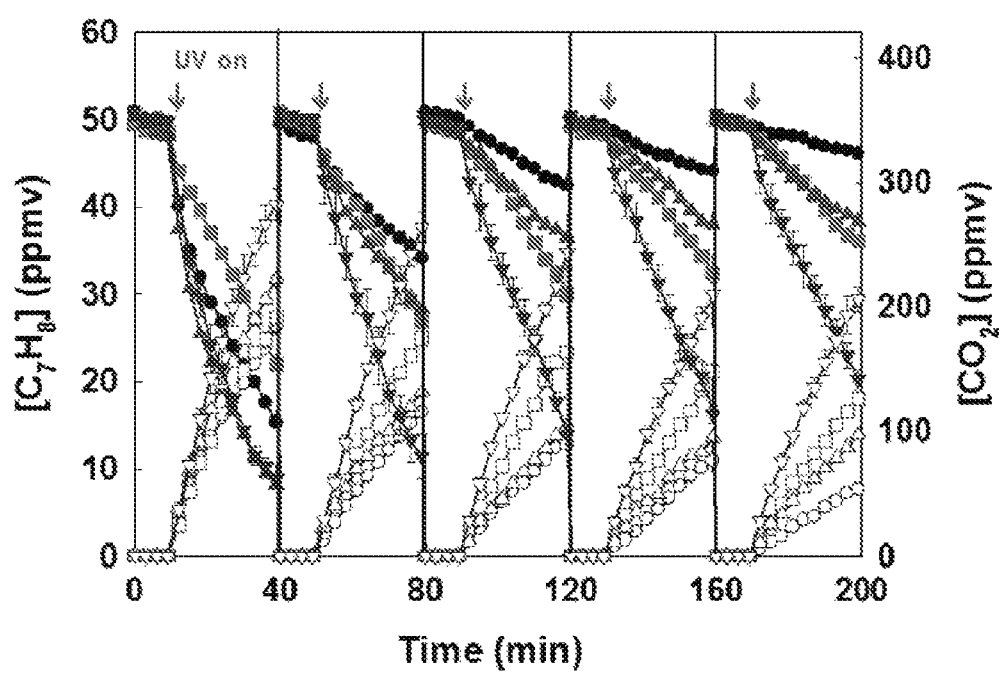
FIG. 7 shows repeated photocatalytic degradation cycles of gas-phase toluene on F—$TiO_2$/Pt (▼), repeated photocatalytic degradation cycles of gas-phase toluene on Pt/$TiO_2$ (▲), repeated photocatalytic degradation cycles of gas-phase toluene on F—$TiO_2$ (■), and repeated photocatalytic degradation cycles of gas-phase toluene on Bare $TiO_2$ (●).

4.2 Photocatalytic Degradation of Gaseous Toluene on Surface-Modified $TiO_2$ Each of Bare $TiO_2$, F—$TiO_2$, Pt/$TiO_2$, and F—$TiO_2$/Pt films was tested as the photocatalyst for air cleaning for degradation of gaseous toluene. To test the durability of each of the photocatalysts, a photocatalytic degradation procedure was performed 5 consecutive times on toluene having an initial concentration of 50 ppmv (FIG. 7). Each degradation cycle was composed of a dark circulation period (10 minutes) for adsorption equilibrium and the following irradiation period (30 minutes) for a photocatalytic reaction. A subsequent degradation cycle was re-started after the air was cleaned out to wash the reactor and the reactor was filled with a fresh gas containing 50 ppmv of toluene. The photocatalytic degradation activities of Bare $TiO_2$, Pt/$TiO_2$, F—$TiO_2$, and F—$TiO_2$/Pt were expressed as pseudo first-order rate constants (Table 1).

TABLE 1

Changes in toluene degradation rate constants of Bare $TiO_2$, Pt/$TiO_2$, F—$TiO_2$, and F—$TiO_2$/Pt during photocatalyst cycles

| | Pseudo first-order rate constants | | | |
|---|---|---|---|---|
| Cycle | $TiO_2$ | Pt/$TiO_2$ | F—$TiO_2$ F | $TiO_2$/Pt |
| 1 | 3.63 (±0.10) | 5.80 (±0.06) | 2.55 (±0.17) | 5.86 (±0.09) |
| 2 | 1.08 (±0.03) | 1.81 (±0.09) | 1.97 (±0.10) | 5.12 (±0.27) |
| 3 | 0.58 (±0.08) | 1.04 (±0.14) | 1.60 (±0.11) | 4.21 (±0.14) |
| 4 | 0.41 (±0.07) | 0.86 (±0.15) | 1.32 (±0.02) | 3.72 (±0.07) |
| 5 | 0.18 (±0.07) | 0.83 (±0.12) | 1.10 (±0.05) | 3.10 (±0.08) |

Figure 8:
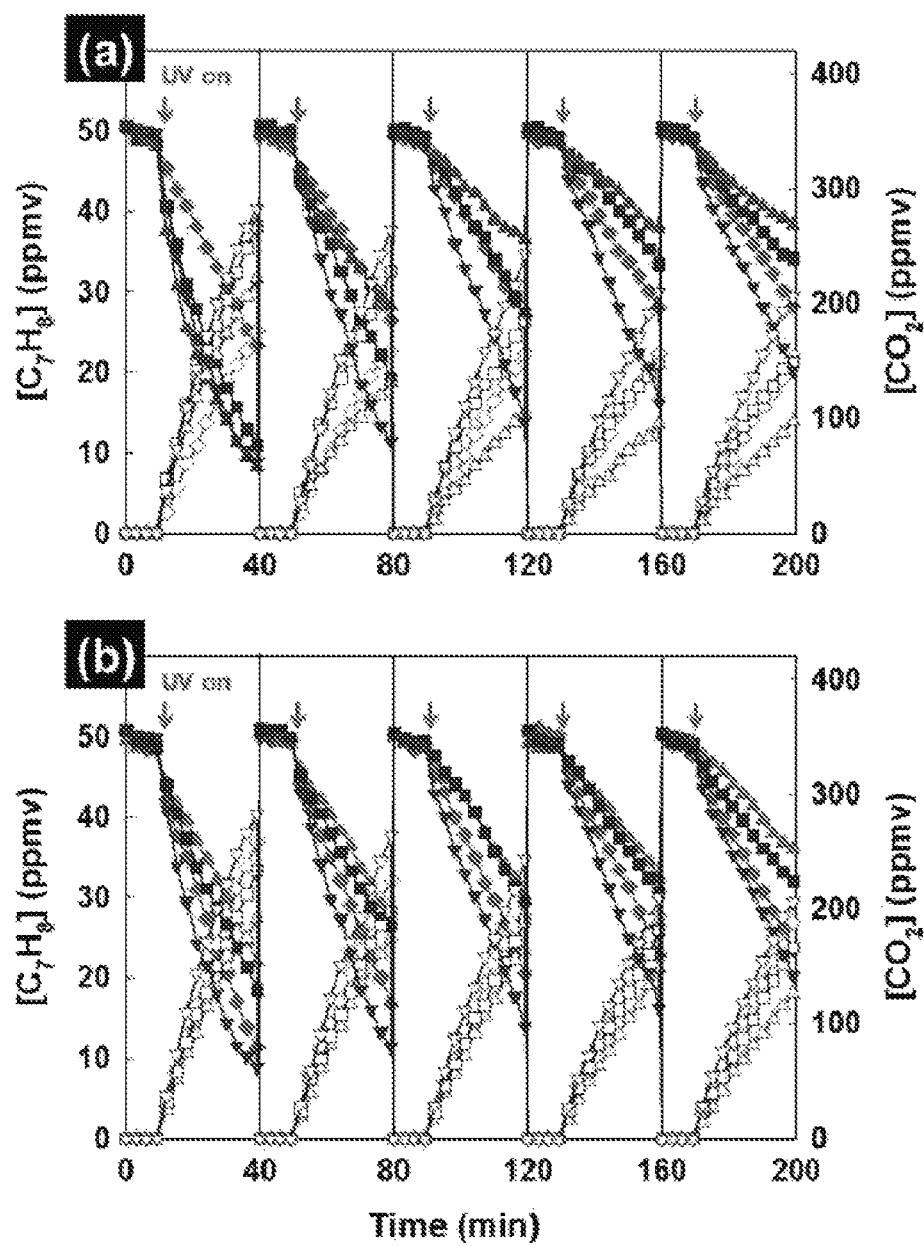
FIG. 8 shows (a) repeated photocatalytic degradation cycles of gas-phase toluene on F—$TiO_2$/Pt performed with a varying loading of fluoride (▲: 0 mM, ■: 10 mM, ▼: 30 mM, and ♦: 50 mM), and (b) repeated photocatalytic degradation cycles of gas-phase toluene on F—$TiO_2$/Pt performed with a varying loading of Pt (▲: 0% by weight, ■: 0.1% by weight, ▼: 0.5% by weight, ♦: 1% by weight).

In the first degradation cycle, the photocatalytic activities of F—$TiO_2$/Pt and Pt/$TiO_2$ were higher than that of Bare $TiO_2$, but the photocatalytic activity of F—$TiO_2$ was lower than that of Bare $TiO_2$. Pt was able to increase the photocatalytic activity of $TiO_2$ for VOC degradation. As the number of degradation cycles increased, the photocatalytic activities of the F—$TiO_2$/Pt and Pt/$TiO_2$ were changed differently. In general, Bare $TiO_2$ and Pt/$TiO_2$ were severely deactivated during the repeated cycles of photocatalytic degradation of toluene (k($TiO_2$) was reduced to less than 5% of the initial value and k(Pt/$TiO_2$) was reduced to less than 15% of the initial value after the fifth cycle). Meanwhile, the degradation activities of F—$TiO_2$ and F—$TiO_2$/Pt were less reduced under the same conditions (k($TiO_2$) was reduced to less than 43% of the initial value and k(Pt/$TiO_2$) was reduced to less than 53% of the initial value after the fifth cycle). FIG. 7 shows that F—$TiO_2$/Pt is the photocatalyst for air cleaning which had high durability while maintaining high photocatalytic activity. For optimization, as shown in FIG. 8, the activities of the F—$TiO_2$/Pt sample were compared with varying concentrations of NaF (10, 30, and 50 mM) and Pt (0.1, 0.5, and 1% by weight). The activity and durability of F—$TiO_2$/Pt for VOC degradation were optimized for 0.5% by weight of Pt and 30 mM fluoride, and the activity was inversely reduced with an increasing amount of Pt or fluoride. All the tested F—$TiO_2$/Pt samples were produced with optimized compositions.

As shown in FIG. 7, $TiO_2$ whose surface was fluorinated was able to hinder the adsorption to delay a specific degradation rate of the VOC, and platinum additionally present on a surface of F—$TiO_2$/Pt was able to extend the lifespan of photo-generated electrons to allow more holes to react with adsorbed water molecules. The adsorption of the degradation intermediates might be hindered by the fluorinated surface of $TiO_2$. As a result, when the surface of $TiO_2$ was modified so that both Pt and F were present on the surface of $TiO_2$, $TiO_2$ was able to exert synergy in preventing the catalytic deactivation caused by accumulation of the degradation intermediates.

Figure 9:
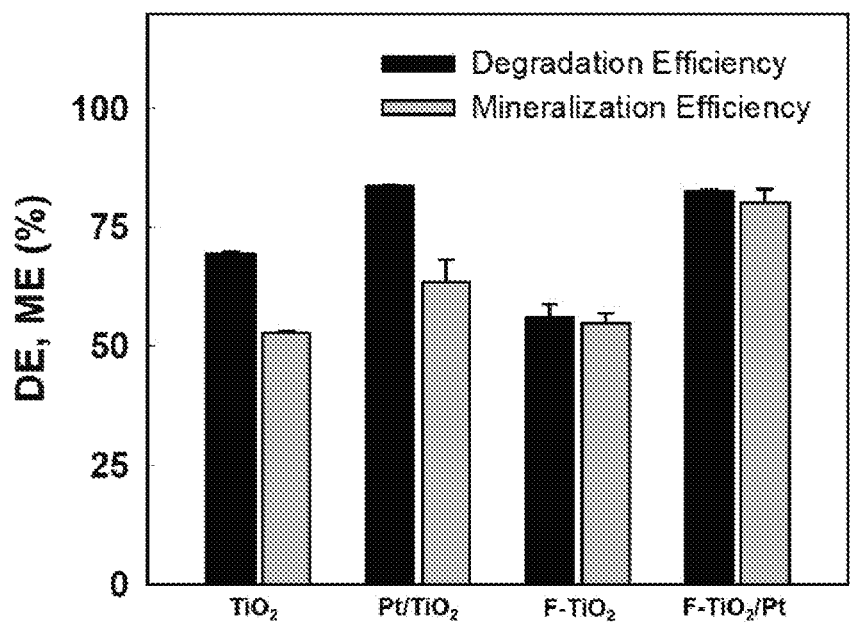
FIG. 9 shows the degradation efficiency (DE) and the mineralization efficiency (ME) of photocatalytic degradation of gas-phase toluene on Bare $TiO_2$, Pt/$TiO_2$, F—$TiO_2$, and F—$TiO_2$/Pt (for a reaction time of 30 minutes).

It is important to understand how the surface modification has an effect on degradation and mineralization of VOCs. There is a different effect of Pt and F on the photocatalytic degradation of gaseous toluene. In the first degradation cycle using each of the photocatalyts, the degradation efficiency (DE=($[C_7H_8]_0$−$[C_7H_8]_{30\ min}$)/$[C_7H_8]_0$×100) and mineralization efficiency (ME=$\Delta_2$/(7×$[C_7H_8]_0$)×100) of toluene were compared (FIG. 9). The photocatalytic DE of Pt-attached $TiO_2$ (Pt/$TiO_2$ and F—$TiO_2$/Pt) increased by 15%, compared to the photocatalytic DE of Bare $TiO_2$. The most important effect of Pt attached to the $TiO_2$ surface is to separate a pair of charges through a Schottky barrier formed at the interface between the $TiO_2$ surface and the Pt nanoparticles. A procedure for separation of charges in Pt/$TiO_2$ occurs for several picoseconds. This rapid charge separation occurs prior to a slow interfacial charge transfer procedure of inducing formation of reactive radical species. Therefore, the efficient charge separation promoted by the presence of Pt allows more charge carriers to produce the reactive radical species. However, both the Bare $TiO_2$ and $Pt/TiO_2$ have ME lower than DE, indicating the toluene degradation intermediates are produced. Meanwhile, the photocatalytic MEs of toluene on the fluorinated $TiO_2$ films (F—$TiO_2$ and F—$TiO_2$/Pt) is very close to the corresponding DEs, indicating that the intermediates are hardly produced on $TiO_2$ whose surface is fluorinated, and the surface fluorination promotes a procedure for mineralizing the VOCs on $TiO_2$.

Figure 11:
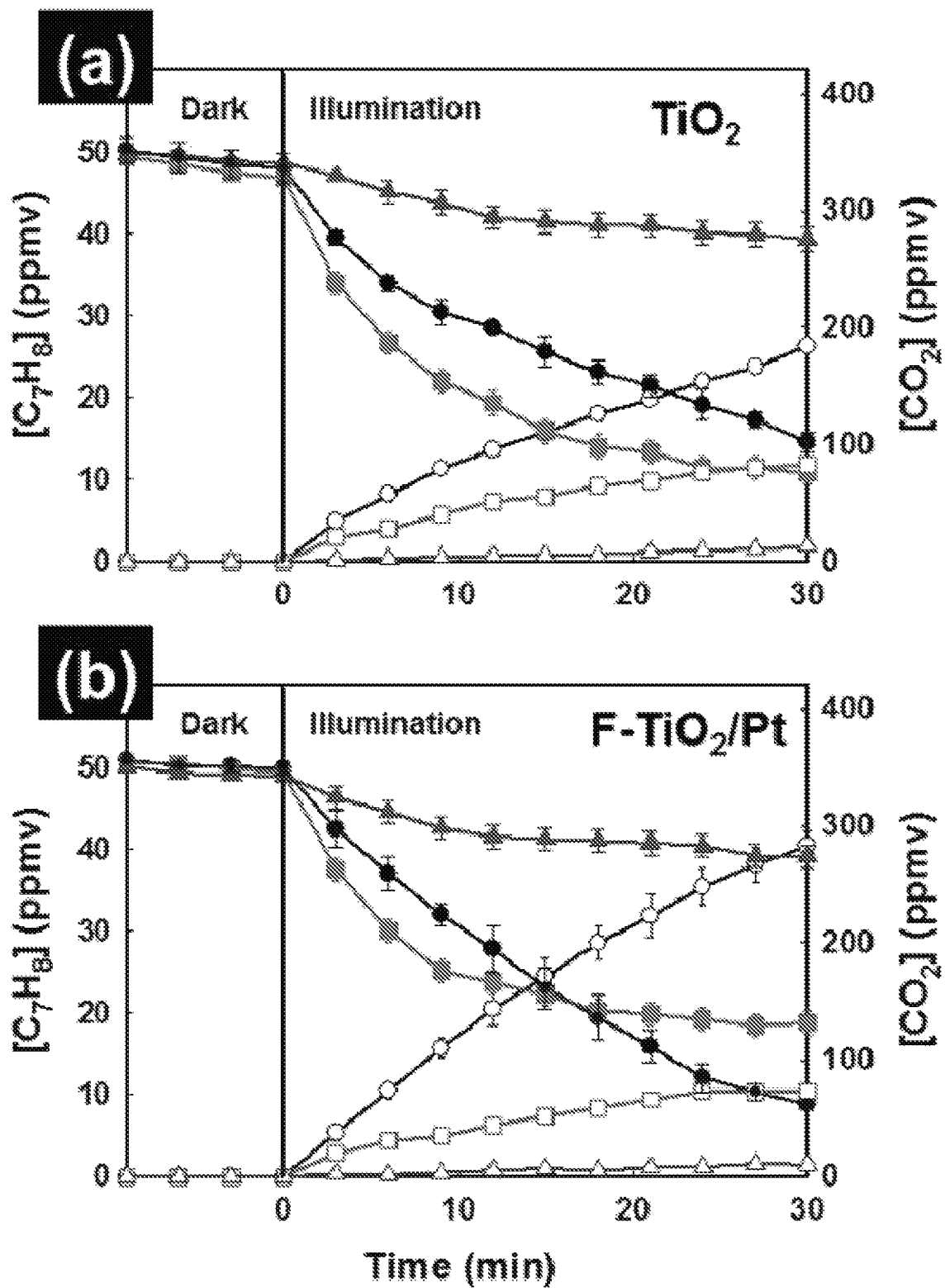
FIG. 11 shows (a) the photocatalytic degradation of gas-phase toluene on Bare $TiO_2$, and (b) the photocatalytic degradation of gas-phase toluene on Pt/$TiO_2$ with the ambient air (65% relative humidity) (●), and without $H_2O$ (■) and $O_2$ (▲).

To examine different mechanical behaviors of Bare $TiO_2$ and F—$TiO_2$/Pt, effects of $O_2$ and water vapor on the photocatalytic degradation activity were compared as shown in FIG. 11. When there is no $O_2$, there is no efficient recipient of CB electrons. Therefore, the photocatalytic degradation of both Bare $TiO_2$ and F—$TiO_2$/Pt was seriously hindered, and thus an amount of $CO_2$ produced was negligible. On the other hand, when there is no $H_2O$ vapor, the initial degradation rates of both Bare $TiO_2$ and F—$TiO_2$/Pt were improved, but the $CO_2$ production was rather suppressed. This pattern may be explained from two competitive effects that (1) $H_2O$ molecules are adsorbed onto a surface of $TiO_2$ to interfere with adsorption sites for toluene molecules, and (2) $H_2O$ molecules are precursors of OH radicals. When the $H_2O$ molecules are not adsorbed, the toluene molecules may easily approach active surface sites, resulting in an improved initial degradation rate. However, when the adsorbed $H_2O$ molecules are in short supply, production of surface OH radicals are inhibited, resulting in degraded mineralization efficiency. An optimal concentration of $H_2O$ vapor may be included in order to maximize the VOC degradation rate. It is noteworthy that a removal rate of toluene on F—$TiO_2$/Pt is rapidly reduced after irradiation for 10 minutes when there is no water vapor. This indicates that the molecularly adsorbed $H_2O$ molecules on F—$TiO_2$/Pt are rapidly depleted when there is no water vapor. This is indirect evidence that the holes preferentially react with the $H_2O$ molecules adsorbed onto the fluorinated surface of $TiO_2$ (Reaction Formula (2)).

4.3 Carbonaceous Deposit Formed on Surface of Photocatalyst

Cresol is produced when OH radicals are added to an aromatic ring of toluene during a photocatalytic degradation of gaseous toluene. Benzyl alcohol, benzaldehyde, and benzoic acid are also produced as toluene degradation by-products. These hydrophilic intermediates are more strongly adsorbed onto the $TiO_2$ surface, compared to the parent toluene molecules. Some of the hydrophilic intermediates may be further modified into condensed products (having a higher molecular weight) as long as they are not rapidly mineralized into $CO_2$. The surface-adsorbed hydrophilic aromatic intermediate (e.g., benzoic acid) may serve as an external recombination site for charge carriers to hinder additional oxidation of the intermediates. Accumulation of the non-biodegradable carbonaceous intermediates on the $TiO_2$ surface blocks active sites, thereby hindering the approach of substrate molecules to the active sites. This is a principal cause of the photocatalytic deactivation.

Figure 12:
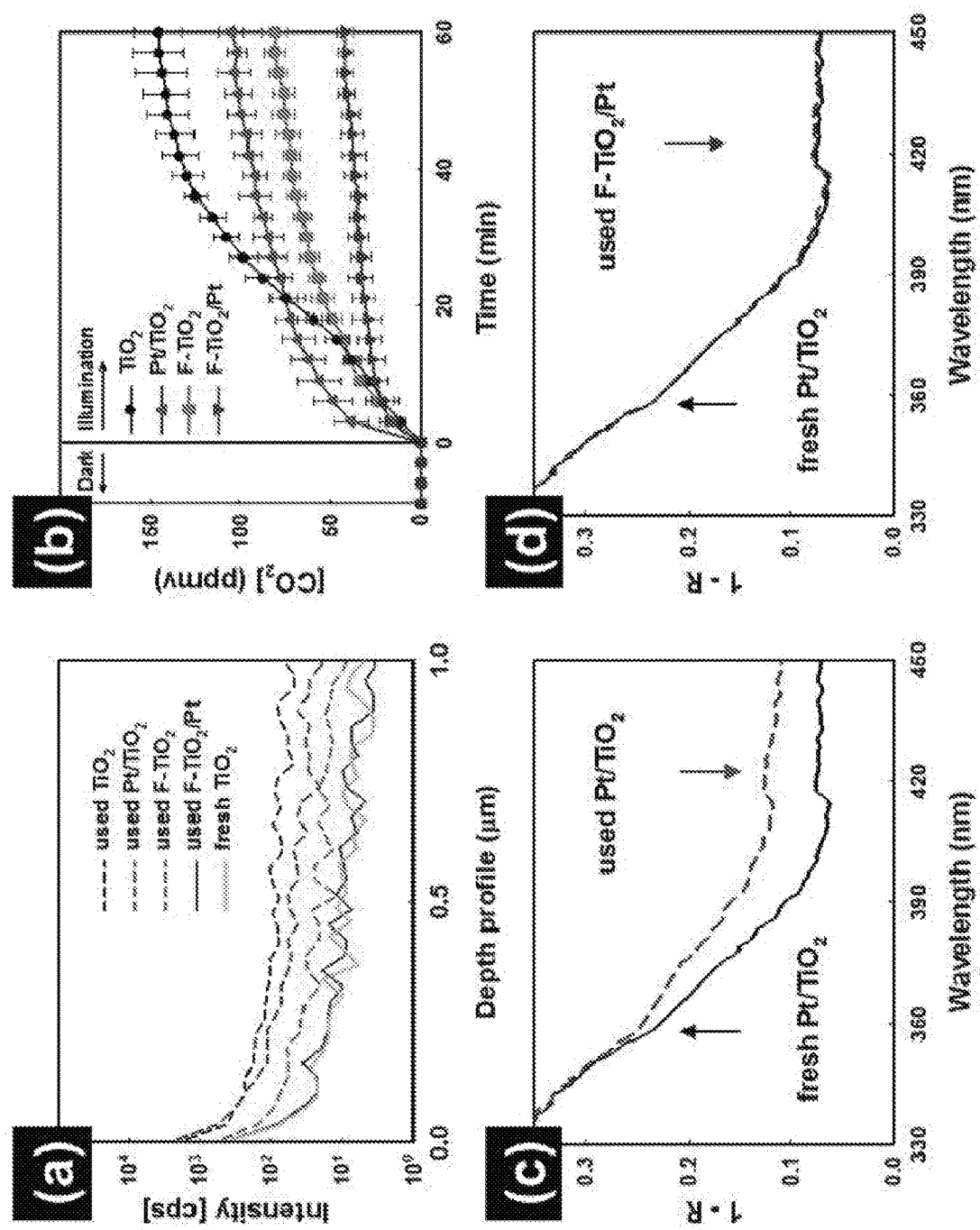
FIG. 12 is a diagram showing (a) carbon signals from the dynamic SIMS depth profiling used Bare $TiO_2$, Pt/$TiO_2$, F—$TiO_2$, and F—$TiO_2$/Pt samples, and fresh $TiO_2$ (after the photocatalytic degradation cycles of toluene; (b) a time profile for $CO_2$ production (in the fresh air without toluene) due to photocatalytic degradation of carbon materials formed on the Bare $TiO_2$, Pt/$TiO_2$, F—$TiO_2$, and F—$TiO_2$/Pt samples; (c) the diffuse reflectance UV-visible absorption spectra of fresh Pt/$TiO_2$ and used Pt/$TiO_2$; and (d) the diffuse reflectance UV-visible absorption spectra of fresh F—$TiO_2$/Pt and used F—$TiO_2$/Pt.

The photocatalyst films (Bare $TiO_2$, $Pt/TiO_2$, F—$TiO_2$, and F—$TiO_2$/Pt) which had been subjected to the photocatalytic degradation of toluene 5 consecutive times were analyzed by dynamic SIMS depth profiling to measure an amount of the carbonaceous deposit on the surfaces of the photocatalysts ((a) of FIG. 12). The carbon signal intensities of the deactivated $TiO_2$ and $Pt/TiO_2$ were clearly higher than that of fresh $TiO_2$, indicating that the surfaces of $TiO_2$ and $Pt/TiO_2$ were covered with a carbonaceous material after the 5 cycles of photocatalytic degradation. The carbon signal intensity was higher at the surface area (<0.5 μm), and was drastically reduced according to the depths of the films because most of the carbonaceous material is present on the surface area. Meanwhile, there was no difference in the carbon signal intensity of the deactivated F—$TiO_2$/Pt, compared to the carbon signal intensity of the fresh $TiO_2$, indicating that the carbonaceous deposit was not present on the surface of F—$TiO_2$/Pt even after the 5 cycles of toluene degradation. To reproduce clean surfaces of the deactivated photocatalyst films ($TiO_2$, $Pt/TiO_2$, F—$TiO_2$, and F—$TiO_2$/Pt), the deactivated photocatalyst films were irradiated with UV rays under the clean air (without toluene) to photocatalytically remove carbonaceous materials. Evolution of $CO_2$ by photocatalytic degradation of the carbonaceous deposits formed in situ was determined as a function of a UV irradiation time ((b) of FIG. 12), which may be used as an indirect method of estimating an amount of the accumulated carbonaceous material. The evolution of carbon dioxide was suddenly increased at an initial stage, and saturated after an hour of UV irradiation. This indicates that most of the carbonaceous deposits present on a surface of the photocatalyst were completely mineralized within an hour of the UV irradiation.

Final concentrations (values measured for oxidized carbon) of the evolved $CO_2$ appeared in the order of $TiO_2$>$Pt/TiO_2$>F—$TiO_2$>F—$TiO_2$/Pt, reconfirming that lowest amount of the carbonaceous deposits were accumulated after the F—$TiO_2$/Pt was subjected to 5 cycles of photocatalytic degradation. This is consistent with the SIMS depth profiling analysis. When the $TiO_2$ surface is deactivated, the color of the $TiO_2$ film turned light brown from white due to the accumulation of the carbonaceous deposits, which can be seen from a change in spectral reflectance. The diffuse reflectance spectrum of the used $Pt/TiO_2$ showed an elevated background at a visible region ((c) of FIG. 12). However, the diffuse reflectance spectrum of the used F—$TiO_2$/Pt was hardly different from those of the fresh samples ((d) of FIG. 12). Also, this reconfirms that the F—$TiO_2$/Pt prevents the accumulation of the carbonaceous deposits during the photocatalytic degradation of toluene.

5.1 Remote Photocatalytic Reaction

The photocatalytic activity mediated by the mobile OH radicals may be closely associated with the resistance to the photocatalytic deactivation. To confirm this, an experimental setup for measuring the "remote" photocatalytic activity (i.e., the activity mediated by the mobile OH radicals) was prepared. In this experiment, reactions of remote stearic acid (SA) and coumarin with remote OH radicals produced on the Bare $TiO_2$ (Comparative Example 1), F—$TiO_2$ (Comparative Example 2), $Pt/TiO_2$ (Comparative Example 3), and F—$TiO_2$/Pt (Example 1) films were tested. An SA solution ($CH_3(CH_2)_{16}COOH$, Aldrich) in methanol (12.5 mM, 80 μL) was dropped on a glass substrate (2×2 $cm^2$), and the methanol solvent was then evaporated to produce an SA-coated film. Meanwhile, coumarin (Aldrich) was dissolved at a concentration of 0.1 g/mL in ethanol. The coumarin solution was spread on the glass substrate (2×2 $cm^2$), and then spin-coated at a rotary speed of 3,000 rpm (in an MIDAS system) for 30 seconds (repeated in triplicate for each coating). After every cycle, the coumarin-coated film was dried at 70° C. for 10 minutes to evaporate the residual ethanol. A coumarin coating procedure was performed 5 times. The SA film (or the coumarin film) and the photocatalyst film were arranged to face each other, and maintained with a small air gap therebetween using a Kapton film having a thickness of 50 μm. The photocatalyst film was prepared into 0.075 g/mL of slurry, which was then made into a photocatalyst membrane having a thickness of 4 to 5 μm, thereby efficiently absorbing incident light. Units of the sandwiched photocatalyst and the SA film (or the coumarin film) were put into a closed circulation reactor, and irradiated with a 370 nm emitting UV-LED.

5.2 Remote Photocatalytic Reaction with Mobile OH Radicals on F—$TiO_2$/Pt

An action of the mobile OH radicals produced on a surface of the photocatalyst was indirectly confirmed by monitoring a reaction with stearic acid (SA; a test substrate) which was not in direct contact with the surface of the photocatalyst. An experimental setup for remote photocatalytic degradation of SA is shown in (a) of FIG. 10. The SA-coated film and the photocatalyst film were arranged to face each other, and maintained with an air gap having a thickness of 50 μm (adjusted using a space). The remote photocatalytic degradation was monitored by measuring a concentration of $CO_2$ produced by degradation of SA at a position remote from the photocatalyst films ($TiO_2$, F—$TiO_2$, Pt/$TiO_2$, and F—$TiO_2$/Pt) under the ambient air ((b) of FIG. 10). F—$TiO_2$/Pt produced a much larger amount of carbon dioxide, compared to the Bare $TiO_2$, Pt/$TiO_2$ and F—$TiO_2$. This means that the F—$TiO_2$/Pt is the most effective in producing the mobile OH radicals mediating the remote photocatalytic degradation. To give more direct evidence supporting the production of the mobile OH radicals on F—$TiO_2$/Pt, coumarin was used as a chemical probe to test a chemical trapping method of OH radicals. Coumarin may selectively react with the OH radicals to produce a coumarin-OH adduct (7-hydroxycoumarin (7-HC); see (c) of FIG. 10). The remote photocatalytic oxidation of coumarin was performed in the same manner as in (b) of FIG. 10. The coumarin-coated film and the photocatalyst film were arranged to face each other, and maintained with an air gap having a thickness of 50 μm. After the ultraviolet irradiation for 3 hours, the fluorescence emission ($\lambda_{em}$=450 nm, $\lambda_{ex}$=332 nm) was measured as coumarin and the reaction products (including 7-HC) were dissolved into ethanol from the glass plate. F—$TiO_2$/Pt showed a clear sign of producing 7-HC (a coumarin-OH adduct) by means of the remote photocatalytic reaction, but Bare $TiO_2$ and Pt/$TiO_2$ showed only a slight sign (see (c) of FIG. 10). F—$TiO_2$ showed a sign of forming 7-HC, confirming the fact that the F—$TiO_2$ produces the mobile OH radicals. When it was assumed that 7-HC was produced at a larger amount in F—$TiO_2$/Pt than in F—$TiO_2$ in the remote photocatalytic experiment, it can be seen that the coexistence of Pt and F species on $TiO_2$ acted synergistically to produce a larger number of OH radicals.

Figure 10:
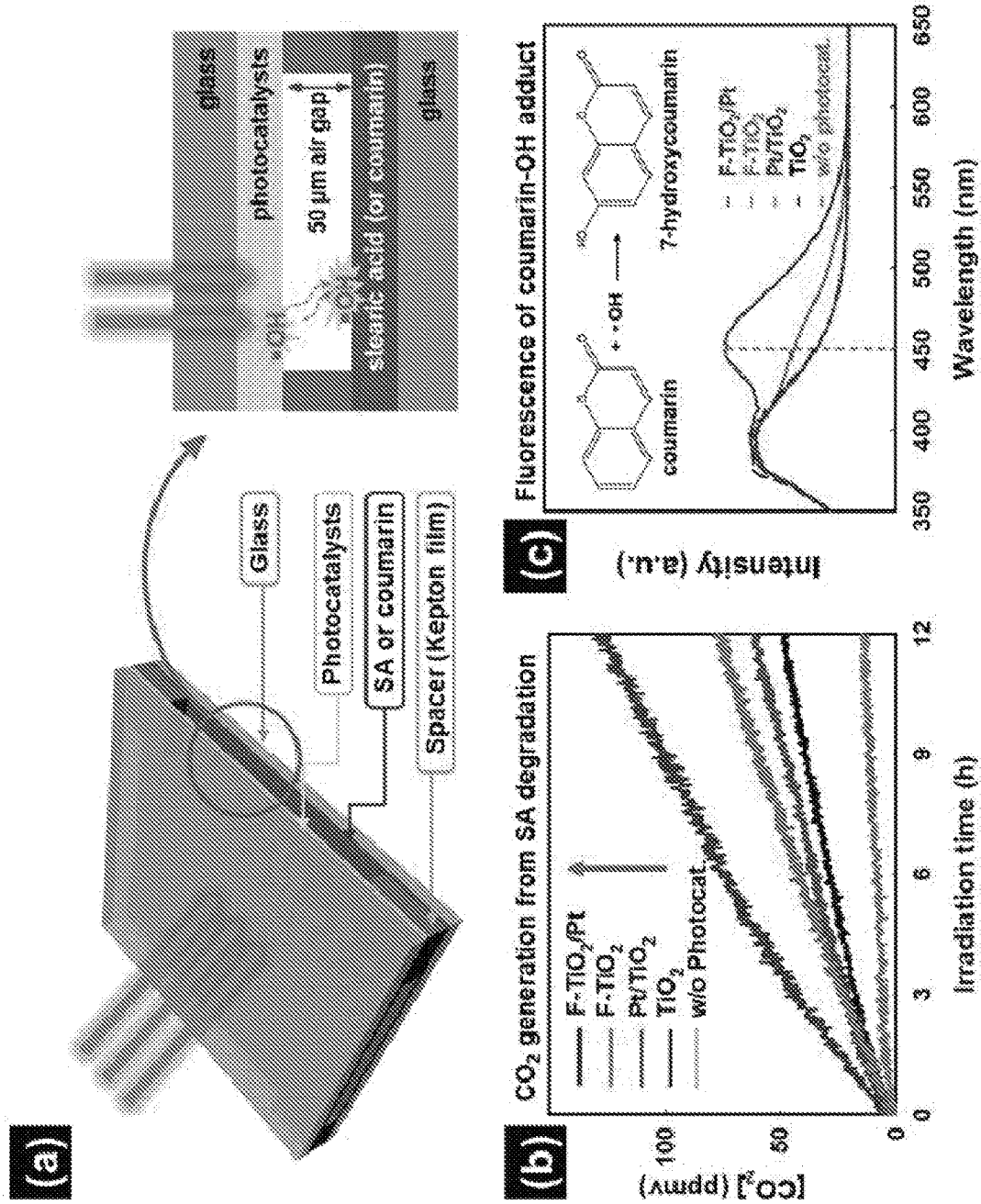
FIG. 10 is (a) a schematic diagram of an experimental setup for a remote photocatalytic reaction of stearic acid (SA) and coumarin, which are not directly contacted with a surface of $TiO_2$, and shows (b) the remote photocatalytic degradation of SA on a glass plate separated from Bare $TiO_2$, Pt/$TiO_2$, F—$TiO_2$ and F—$TiO_2$/Pt films. The production of carbon dioxide is monitored to evaluate degradation of SA; and (c) a coumarin-OH adduct (7-hydroxycoumarin; 7-HC) is produced through a reaction of coumarin and a hydroxyl radical using a remote photocatalytic oxidation reaction on coumarin (see an insert diagram). The production of 7-HC is monitored by measuring the fluorescence emission spectra ($\lambda_{em}$=450 nm, $\lambda_{ex}$=332 nm) obtained after performing a remote photocatalytic reaction on the Bare $TiO_2$, Pt/$TiO_2$, F—$TiO_2$, and F—$TiO_2$/Pt films for 3 hours.

The average lifespan (τ) of the OH radicals in the ambient conditions is approximately 0.01 to 1 second (s). This is affected by a concentration of reactive gas components such as $O_3$, VOCs, and NOx. Because remote photocatalytic experiments using various photocatalysts were performed in the same experimental conditions, the mobile OH radicals should have the same lifespan in a gas phase, regardless of the type of the photocatalysts. The typical gas diffusion coefficients of the photocatalysts under the ambient conditions are in a range of 0.1 to 0.2 $cm^2s^{-1}$. As a result, there are movable OH radicals, the OH radicals may move a gap distance of 50 μm according to the roughly estimated diffusion length (L). When τ=0.01 s, the rough diffusion length L is: $[(0.1\ cm^2s^{-1})*(0.01\ s)]^{0.5}$=0.32 mm, or when τ=1 s, the rough diffusion length L is 0.32 cm. In both cases, the rough diffusion length L was much longer than 50 μm. Therefore, when the OH radicals were detached in the form of a gas phase from the irradiated surface of the photocatalyst, the OH radicals were able to diffuse through the air by a distance of approximately 1 mm. As can be seen in FIG. 10, the production of such mobile OH radicals increased to a very high extent because both of Pt and F species were attached onto the surface of $TiO_2$. The mobile OH radicals were more effective in degrading and mineralizing the non-biodegradable substrate and the intermediates thereof, indicating that this is associated with why the F—$TiO_2$/Pt is more resistant to the deactivation.

The surface-modified titanium dioxide according to the various embodiments as described above has characteristics such as catalyst deactivation resistance during the photocatalytic degradation of VOCs.

In particular, it is important to prevent formation of the non-biodegradable intermediates or carbonaceous deposits on a surface of the photocatalyst in order to prevent the photocatalyst from being deactivated during the VOC degradation procedure. In this case, the surface fluorination promotes production of the mobile OH radicals while interfering with adsorption of VOCs and degradation intermediates thereof. F—$TiO_2$ was less deactivated, but had an initial photocatalytic degradation activity lower than the Bare $TiO_2$.

Pt on the surface of the photocatalyst enhanced the lifespan of the charge carriers by allowing more holes to react with the adsorbed water molecules to produce movable OH radicals. When toluene was used as a target substrate, Pt/$TiO_2$ showed a photocatalytic degradation activity higher than the Bare $TiO_2$. However, Pt/$TiO_2$ undergone sudden deactivation during a repeated degradation procedure.

F—$TiO_2$/Pt had the highest photocatalytic activity and durability to the toluene degradation. The surface fluorination for replacing hydroxyl groups on the surface of $TiO_2$ may promote formation of the mobile OH radicals instead of the surface-attached OH radicals. Surface platinization improves the lifespan of charge carriers and allows more holes to efficiently react with the adsorbed water molecules. It can be seen that the F—$TiO_2$/Pt film produced the largest number of the mobile OH radicals by means of the remote photocatalytic oxidation reaction of coumarin with stearic acid coated onto the glass plate which was separated by a small air gap (50 μm) from the photocatalyst film. The photocatalytic oxidation mediated by the mobile OH radicals efficiently interfered with deposition of the carbonaceous intermediates on the surface of F—$TiO_2$/Pt, and enhanced the mineralization efficiency of VOCs, thereby improving durability of the photocatalyst during the VOC degradation.

As a result, a larger number of the mobile OH radicals may be produced by combining the surface fluorination and platinization on $TiO_2$, thereby improving high resistance to the remote photocatalytic oxidation (mediated by the mobile OH radicals) and the catalytic surface deactivation. The photocatalyst (F—$TiO_2$/Pt) modified with both the components has high DE and ME of VOCs and excellent durability, compared to the other photocatalysts ($TiO_2$, F—$TiO_2$, and Pt/$TiO_2$).

Although preferred embodiments of the disclosure have been shown and described above, it will be apparent that the disclosure is not limited the aforementioned specific embodiments, and various changes and modifications can be made by those skilled in the art to which the disclosure pertains without departing from the scope of the disclosure as defined in the claims. Also, it should be understood that such changes and modifications are not intended to be independently interpreted from the spirit or scope of the disclosure.

The invention claimed is:

1. A method for producing a photocatalyst for air cleaning, the method comprising the steps of:
preparing titanium dioxide ($TiO_2$);
attaching platinum to a surface of the titanium dioxide by a photodeposition method;
mixing the platinum-attached titanium dioxide in the powder form with a volatile solvent to prepare a paste;
spreading the paste on a substrate;
drying the paste on the substrate; and
producing a surface-modified titanium dioxide by replacing a hydroxyl group in the platinum-attached surface of the titanium dioxide with a fluoro by putting the dried paste spreaded susbstrate into a fluoride solution for a predetermined period of time,
wherein the photodeposition method comprises:
adding chloroplatinic acid (H2PtC16) serving as a platinum precursor, and methanol serving as an electron donor to an aqueous suspension of $TiO_2$; and
irradiating the aqueous suspension of $TiO_2$ including the chloroplatinic acid (H2PtC16) and the methanol with ultraviolet rays, and wherein the fluoride solution is a KF solution or an HF solution.

2. The method of claim 1,
wherein, in the attaching of the platinum to the surface of the titanium dioxide, the platinum is attached to the surface of the titanium dioxide using a photodeposition method, and
wherein, in the producing of the surface-modified titanium dioxide, the platinum-attached titanium dioxide is put into a fluoride solution to attach the fluoro to the platinum-attached surface of the titanium dioxide.

3. The method of claim 1,
wherein the prepared titanium dioxide is in a powder form, and
wherein, in the attaching of the platinum to the surface of the titanium dioxide, the platinum is attached to the surface of the titanium dioxide in the powder form using a photodeposition method.

4. The method of claim 3, further comprising the steps of:
mixing the platinum-attached titanium dioxide in the powder form with a volatile solvent to prepare a paste; and
spreading the paste on a substrate and then drying the substrate,
wherein, in the producing of the surface-modified titanium dioxide, the dried substrate is put into a fluoride solution.

5. The method of claim 1, further comprising manufacturing the produced surface-modified titanium dioxide into a bead shape.

6. The method of claim 1, further comprising coating a porous material with the obtained surface-modified titanium dioxide.

* * * * *